United States Patent [19]

Yeo et al.

[11] Patent Number: 5,122,407
[45] Date of Patent: Jun. 16, 1992

[54] ODOR-REMOVING COVER FOR ABSORBENT PADS AND METHOD OF MAKING SAME

[75] Inventors: Richard S. Yeo, Dunwoody; Mary G. Weber, Alpharetta; Stephanie R. Majors, Grayson, all of Ga.; Richard W. Tanzer, Neenah, Wis.

[73] Assignee: Kimberly-Clark Corporation, Neenah, Wis.

[21] Appl. No.: 540,714

[22] Filed: Jun. 20, 1990

[51] Int. Cl.$^5$ .............................. B32B 27/14
[52] U.S. Cl. ................... 428/138; 428/198; 428/264; 428/265; 428/290; 428/74; 428/283; 604/359
[58] Field of Search ............... 428/198, 264, 265, 290, 428/905, 138; 604/359

[56] References Cited

U.S. PATENT DOCUMENTS

| | | | |
|---|---|---|---|
| 795,562 | 7/1905 | Tatti | 604/356 |
| 2,024,145 | 12/1935 | Cline | 167/84 |
| 2,066,946 | 1/1937 | Reiman | 167/84 |
| 2,690,415 | 9/1954 | Shuler | 167/84 |
| 3,068,187 | 12/1962 | Bolstad et al. | 260/29.6 |
| 3,108,018 | 10/1963 | Lewis | 117/161 |
| 3,149,023 | 9/1964 | Bodendorf et al. | 125/113 |
| 3,340,875 | 9/1967 | Dudley et al. | 128/290 |
| 3,439,678 | 4/1969 | Thomas | 128/284 |
| 3,542,028 | 11/1970 | Beebe et al. | 128/290 |
| 3,670,731 | 6/1972 | Harmon | 128/284 |
| 3,683,917 | 8/1972 | Comerford | 128/287 |
| 3,693,622 | 9/1972 | Jones, Sr. | 128/290 R |
| 3,804,094 | 4/1974 | Manoussos et al. | 604/359 |
| 3,856,014 | 12/1974 | Yamauchi | 128/290 |
| 3,903,889 | 9/1975 | Torr | 128/287 |
| 3,939,838 | 2/1976 | Fujinami et al. | 604/359 |
| 3,995,636 | 12/1976 | Murray et al. | 604/359 |
| 4,055,184 | 10/1977 | Karami | 128/287 |
| 4,066,394 | 1/1978 | Leonard | 8/137 |
| 4,169,187 | 9/1979 | Glazar | 428/418 |
| 4,194,041 | 3/1980 | Gore et al. | 428/315 |
| 4,208,459 | 6/1980 | Becker et al. | 428/154 |
| 4,217,386 | 8/1980 | Arons et al. | 428/198 |
| 4,226,237 | 10/1980 | Levesque | 128/285 |
| 4,289,513 | 9/1981 | Brownhill et al. | 55/387 |
| 4,296,166 | 10/1981 | Ogino | 428/283 |
| 4,347,844 | 9/1982 | Ohki et al. | 128/287 |
| 4,381,784 | 5/1983 | Aberson et al. | 605/368 |
| 4,397,646 | 8/1983 | Daniels et al. | 604/381 |
| 4,429,001 | 1/1984 | Kolpin et al. | 428/283 |
| 4,431,698 | 2/1984 | Case et al. | 428/244 |
| 4,433,024 | 2/1984 | Eian | 428/198 |
| 4,459,332 | 7/1984 | Giglia | 428/86 |
| 4,467,013 | 8/1984 | Baldwin | 428/289 |
| 4,508,775 | 4/1985 | Adiletta | 428/240 |
| 4,525,410 | 6/1985 | Hagiwara et al. | 428/198 |
| 4,544,650 | 10/1985 | Kinder et al. | 502/424 |

(List continued on next page.)

FOREIGN PATENT DOCUMENTS

| | | |
|---|---|---|
| 109904 | 11/1939 | Australia . |
| WO81/01643 | 6/1981 | European Pat. Off. . |
| 2424988 | 11/1975 | Fed. Rep. of Germany . |
| 652088 | 11/1976 | Fed. Rep. of Germany . |
| 302984 | 2/1984 | Fed. Rep. of Germany . |
| 2093352A | 2/1982 | United Kingdom . |
| 2093551A | 2/1982 | United Kingdom . |

Primary Examiner—George F. Lesmes
Assistant Examiner—Kathryne Shelborne
Attorney, Agent, or Firm—Joseph P. Harps

[57] ABSTRACT

An absorbent pad has a cover formed of non-woven fibrous material, which is coated with a fluorocarbon polymer and odor absorber(s). The cover sheet is apertured around a critical zone to overcome undesired surface tension effects. The method of producing the cover includes providing a water-based mixture that includes 1% by weight of a fluorocarbon composition. An odor absorbing reagent is added to the mixture which then is applied to a nonwoven web of fibrous material. The treated web is dried to remove the excess water from the mixture, and the fluorocarbon composition component is cured to form a hydrophobic coating around the reagent and to bind the reagent to the web. The drying and curing steps can be accomplished by applying a flow of air heated to a temperature in a range from about 100° C. to about 120° C. to the web until the water has been removed.

35 Claims, 1 Drawing Sheet

U.S. PATENT DOCUMENTS

| | | | |
|---|---|---|---|
| 4,545,080 | 10/1985 | Gorham | 2/54 |
| 4,547,195 | 10/1985 | Jackson | 604/359 |
| 4,565,727 | 1/1986 | Giglia et al. | 428/172 |
| 4,583,980 | 4/1986 | Schneider et al. | 604/359 |
| 4,650,479 | 3/1987 | Insley | 604/358 |
| 4,655,757 | 4/1987 | McFarland et al. | 604/366 |
| 4,677,019 | 6/1987 | Von Blucher | 428/244 |
| 4,699,620 | 10/1987 | Bernardin | 604/385 |
| 4,701,177 | 10/1987 | Ellis et al. | 604/385 A |
| 4,702,749 | 10/1987 | Sircar et al. | 55/33 |
| 4,715,857 | 12/1987 | Juhasz et al. | 604/359 |
| 4,721,647 | 1/1988 | Nakanishi et al. | 428/283 |
| 4,732,805 | 3/1988 | Maggs | 428/327 |
| 4,748,065 | 5/1988 | Tanikella | 428/152 |
| 4,755,178 | 7/1988 | Insley et al. | 604/367 |
| 4,795,562 | 1/1989 | Walsh | 210/232 |
| 4,806,408 | 2/1989 | Pierre et al. | 428/138 |

ODOR-REMOVING COVER FOR ABSORBENT PADS AND METHOD OF MAKING SAME

BACKGROUND OF THE INVENTION

The present invention relates to an improved cover for an absorbent personal care product and to the products using such cover. More particularly, the invention relates to the cover for a feminine pad and to pads using such cover. Absorbent pads designed to be worn by humans to absorb bodily fluids, such as urine, menstrual fluid, perspiration, etc., include such articles as disposable diapers, sanitary napkins, panty shields, underarm shields, and incontinence pads. In use, these articles release malodorous vapors. Various compounds, chemicals, mixtures, and like materials (i.e., absorbents such as activated carbon, clay, and zeolites) are known to combat some of these malodorous compounds. Odor absorbents such as activated carbon have been incorporated into sheet materials or fabrics for use in protective articles and clothing. Additionally, because some odor absorbent agents are less effective once they have become wetted, various methods have been employed to minimize the exposure of the odor absorbents to moisture. These methods include: locating the odor absorbents outside of the liquid absorbent layer(s) of the products, protecting the absorbents with liquid impermeable/vapor permeable sheet materials, sandwiching the odor absorbents between two protective layers, hydrophobically coating the absorbents with various compounds to render them liquid impermeable, etc. Particular examples are discussed below.

U.S. Pat. No. 4,732,805 to Maoos discloses an active carbon material that is coated with a gas permeable surface of particulate hydrophobic material which preferably is a fluorocarbon resin such as polytetrafluoroethylene (PTFE). The active carbon can be in the form of a fabric known as charcoal cloth or a felted material, and in such cases the hydrophobic material is present in a range from about 5 to 10% by weight of the active carbon. The coating of fluorocarbon resin protects the activated carbon from absorbing water while allowing the undesirable vapors to permeate through the resin and be adsorbed by the activated carbon. To apply the coating, the activated carbon material is preferably immersed in an aqueous suspension of the hydrophobic material and then dried by applying a flow of air heated to a temperature around 100° C. The hydrophobic material may be present in the suspension in a preferred that the hydrophobic material be present at a concentration of at least 1.5% by weight. When the hydrophobic material is polytetrafluoroethylene, the suspension preferably is stabilized by an anionic wetting agent, but Maoos prefers that no binder or other component is included. The particle size of the hydrophobic material in suspension preferably is between micron and 0.01 micron, with a mean particle size preferably of one tenth of a micron.

U.S. Pat. No. 3,939,838 to Fujinami, et al discloses an article for treating menstrual fluid which employs a cover member forming an enclosure, an absorbent layer positioned within the enclosure for absorbing the menstrual fluid, a water-proofing layer also positioned within the enclosure for preventing the fluid from permeating to the outside of the cover member, and a deodorizer composition such as active carbon and the like located within the enclosure and having the function of absorbing and holding the menstrual fluid and simultaneously removing the odor released from the menstrual fluid. Active carbon, active silica, active alumina, ion exchange resin, chlorophyll, and the like are used as the deodorizers. The deodorizer is contained in sheets that are made of cellulose fiber. The deodorizer sheets can be interposed between the respective absorbent layers and the respective water-proofing layers, or in the absorbent layer and/or in the water-proofing.

U.S. Pat. No. 3,693,622 to Jones discloses waste fluid absorption devices, including sanitary napkins and tampons, comprising a coplanar multiple ply of thin absorbent tissue paper impregnated in selected exterior border areas with non-toxic, waste fluid repellent compositions. Typically, the repellent impregnant can be non-volatile polyfluorocarbon fluids; non-volatile dimethyl polysiloxane fluids; non-volatile hydrocarbon oil fluids; non-volatile fluid long chain fatty acid alkyl esters, and non-volatile mono-, di-, and tri-glyceride esters of long chain fatty acids.

U.S. Pat. No. 4,467,013 to Baldwin discloses non-woven bioactive, water and alcohol-repellent medical fabrics provided with a bioactive finish which is substantive on the fabric and is able to destroy migrating and cross-contaminating bacteria, algae and fungi. Specifically, a process for preparing a water and alcohol repellent, bacteriostatic non-woven medical substrate includes applying a solution of a specific silicone quaternary amine together with a water-repelling fluorocarbon and a wax/resin fluorocarbon extender, to produce the desired repellent surface. The fluorocarbon repellent component is typically a dispersion of fluoropolymer in water.

U.S. Pat. No. 3,068,187 to Bolstad discloses segmented fluorine-containing copolymers useful for imparting repellency to oil and water and resistance to soiling to a variety of substrates. Fibrous, porous and continuous surfaces may be treated with these segmented polymers. The segmented copolymers may be applied as a surface treatment by known methods of coating such as spraying, brushing or impregnation from an aqueous or organic solvent dispersion or an organic solvent solution of the segmented copolymer.

U.S. Pat. No. 3,683,917 to Comerford discloses a product for absorbing and retaining body fluids comprising a cellulosic absorbent body or core, a cellulosic covering, and a biodegradable, water impervious barrier sheet or layer which comprises a water repellent material deposited on a cellulosic tissue. Among such water repellent materials are: various fluorocarbons such as PTFE, CTFE, FEP, etc.; "Scotchguard" Repellents FC-208, FC-210, FC-212, FC-214, etc.; silicones such as Dri-Film 1040, a methyl hydrogen polysiloxane and Dri-Film 1042 and 1043, modified methyl hydrogen polysiloxanes; cationic starch type water repellents such as "Cyansize" (American Cyanamid) and "Aquapel", a ketone dimer emulsified with a cationic starch, sold by Fancourr Co.; etc.

U.S. Pat. No. 4,565,727 to Giolia, et al discloses an air and water vapor permeable, toxic vapor absorptive non-woven fabric material comprising a wet-laid sheet containing fibrillated acrylic fiber, and an activated carbon constituent selected from the group consisting of activated carbon fiber, activated carbon particles, and mixtures of activated carbon fiber and activated carbon particles. The material is produced via the wet-laying process, utilizing fibrillated acrylic fibers as the binder material, whereby the material is prepared by wet-laying the activated carbon constituent and fibrillated acrylic fibers from a water suspension thereof.

U.S. Pat. No. 4,217,386 to Arons, et al discloses a laminated, highly sorbent, active carbon fabric which is permeable to water vapor while sorbing substantial quantities of toxic chemical vapors, and process of making such a laminated fabric. Arons, et al is concerned with the formation of a multilayered, usually five-layered, laminated structure comprising: an inner woven fabric made of yarns of active carbon, produced by carbonizing high polymer yarns forming the fabric and thereafter activating the carbon; two outer layers (webs) of spunbonded non-woven fabric, prepared from continuous filaments of a high polymer; and two intermediate layers (mats), one on each side of the active carbon fabric. The final five layered, laminated fabric structure is produced by superimposing the layers as described above and fusion welding the five layers together over spaced apart areas. The woven active carbon fabric of the invention may be prepared by spinning high polymer yarns of various types, such as regenerated cellulose yarns of various conventionally produced types, polyacrylonitrile yarns, phenol-formaldehyde yarns, pitch yarns, or other suitable high polymer yarns, weaving such yarns into fabrics, carbonizing the fabrics, and activating the carbonized fabrics, all accomplished conventionally.

U.S. Pat. No. 4,459,332 to Giolia discloses an air and water vapor permeable, toxic vapor absorptive fabric material. The toxic vapor absorptive ingredient is activated carbon fiber flocking having deposited in the voids formed therebetween, activated carbon powder. The invention comprises, in superimposed relationship: (a) a first inactive, woven or non-woven fabric; (b) a first air and water vapor permeable adhesive layer having activated carbon fiber flocking positioned on the surface thereof away from the first inactive fabric and activated carbon powder deposited in the voids formed between the flocking; (c) a second air and water vapor permeable adhesive layer and; (d) a second inactive layer of woven or non-woven fabric. The materials which form components (b) and (c) are produced from water vapor and air permeable adhesives preferably in the form of a foam. Component (b) is prepared by first coating the fabric material (a) with the adhesive foam. The side coated with the adhesive is then flocked with the activated carbon fibers. The activated carbon fibers are deposited upon the foam adhesive side of the coated fabric (a) by any known mechanical flocking method, preferably before the adhesive is heat cured. The fiber flocking is usually sprinkled on top of the foam adhesive coating. To the flocked side of the fabric is then added activated carbon powder while a vacuum is applied from the fabric side to draw the powder into the voids between the flocked carbon fibers.

U.S. Pat. No. 3,439,678 to Thomas discloses a plied fabric having high water resistance and comprising at least two layers, each formed from a woven fabric which is resistant to standing water and is air and water vapor permeable. The fabrics are composed of fibers which are hydrophobic in themselves or are composed of fibers which subsequently are rendered hydrophobic by suitable coating means. One type of coating composition deemed especially suitable by Thomas is the fluoro chemical type textile finish which is marketed by Minnesota Mining & Manufacturing Co. (a.k.a. 3M Company) under the SCOTCHGARD ® trademark. The coating composition may be applied by any well known method such as padding, spraying, immersion, or the like.

U.S. Pat. No. 3,995,636 to Murray, et al discloses a catamenial device such as a tampon which comprises a segment of a rapidly re-expandable hydrophilic polymeric foam held in compression by a constraining means. The constraining means comprises a coating material that includes a mixture of sodium bicarbonate and citric acid. The coating material may be provided by the application of a solution to the surface of the foam segment, or by full impregnation. Murray, et al discloses that the restoration of a slightly acidic environment in the vaginal area prevents the undue accumulation of noxious odor and irritation which results from the enzymatic reduction of the uric acid, urea, amino acids and the like to ammonia and volatile amines.

U.S. Pat. No. 4,508,775 to Adiletta discloses a flexible, microporous, hydrophobic and oleophobic film-like composite structure comprising from about 25 to about 75 parts by weight of inorganic reinforcing microfibers, particularly glass, and from about 75 to about 25 parts by weight of a polymeric binding agent, preferably a copolymer of ethylene and vinyl acetate. A treating agent, preferably a fluorinated hydrocarbon, is present in an amount sufficient to render the composite structure hydrophobic and oleophobic. Alternatively, the treating agent may be combined with the microfibers and binding agent in the slurry prior to laydown and formation of the sheet material. The composite structure may be used in combination with a carbon or chemical liner in protective clothing, in which case it may be desirable to protect the carbon liner layer from body perspiration by laminating an abrasion resistant layer of material, such as a non-woven, spun bonded monofilament polyester, to the charcoal liner on the side opposite the composite structure.

U.S. Pat. No. 4,194,041 to Gore. et al discloses a water-proof article that prevents liquid water from penetrating through to undergarments while at the same time permitting moisture vapor to pass out through the article. The article is layered: a microporous hydrophobic outer layer which permits the passage of moisture vapor but resists penetration by liquid water at pressures up to about 345 kiloNewtons per meter squared ($kN/M^2$); a hydrophilic inner layer permitting the transfer of moisture vapor but preventing surface tension lowering agents such as those contained in perspiration and/or body oils from reaching the hydrophobic layer. Gore, et al discloses that a film of porous, expanded polytetrafluoroethylene, which has been heated above its crystalline melt point after expansion, has been found to be an ideal hydrophobic layer for rainwear applications. These films are highly porous yet the pores are very small in size. The latter fact results in high water entry pressure. Other hydrophobic materials for use in the outer layer include highly crystalline films of expanded PTFE, which have been heated above their crystalline melt point, and films of other microporous hydrophobic polymers such as polypropylene.

U.S. Pat. No. 4,169,187 to Glazar discloses a powder coating composition of epoxy resins obtained by blending two types of epoxy resins with a curing agent. One resin is of the epichlorohydrin-bisphenol-A-type. The other resin is an epichlorohydrin-bisphenol-A modified with an epoxy-novolac. The Glazer patent discloses using the mixture for coating the interior of food and beverage containers and for a lining in hot-water services when finely divided polyvinylidine fluoride powder is added for hydrophobicity.

OBJECTS AND SUMMARY OF THE INVENTION

It is an object of the present invention to provide an improved feminine pad.

A further object of the present invention is to provide an absorbent pad cover having a lasting deodorant effect.

It is another object of the invention to provide an absorbent pad having a cover which is stain-free, clean, and dry when in use.

Still another object of the invention is to provide an improved nonwoven pad cover having deodorants which adhere strongly to the nonwoven base substrate. A related object is to provide an improved pad having deodorant particles which do not come loose during handling and usage.

Yet another object of the invention is to provide an absorbent pad which improves the utilization of odor absorber(s) by providing same in a pad cover, yet protects the odor absorber(s) against the contamination by bodily fluids such as menses during usage.

A further object of the invention is to provide an improved absorbent pad in which the deodorant is disposed so that the deodorant properties are durable over the life of the product and exhausted only in the process of removing and/or neutralizing odor causing vapors.

Additional objects and advantages of the invention will be set forth in part in the description which follows, and in part will be obvious from the description, or may be learned by practice of the invention. The objects and advantages of the invention may be realized and attained by the methods and combinations particularly pointed out in the appended claims.

To achieve the objects and in accordance with the purpose of the invention, as embodied and broadly described herein, the odor absorbing cover for an absorbent pad comprises a nonwoven web of fibrous material, a fluorocarbon polymer composition adhered to the fibers throughout the web, an odor absorbing reagent bound to the web by the fluorocarbon composition and rendered hydrophobic thereby, and a plurality of apertures defined through the web. One portion of the surface of the web defines a critical zone in which the number of apertures per square inch ranges from about 6 apertures to about 1100 apertures.

The diametric size of the apertures preferably is in the range of from about 1 millimeter to about 2 millimeters, but can be in the range of from about 0.8 millimeters to about 10 millimeters. Moreover, the aperture density in the critical zone preferably ranges from about 50 apertures per square inch to about 300 apertures per square inch. In addition, the percent of the critical zone that constitutes open area preferably ranges from about 10% to about 40%, but can range from about 2% to about 90%.

The material used to form the nonwoven web preferably is chosen from the group of fibers that includes polyester fibers, polyamide fibers, cellulosic fibers, and polyolefin fibers. Suitable polyolefin fibers include polypropylene fibers, polyethylene fibers, polybutylene fibers, etc. The nonwoven web preferably is formed as a spunbond web, or a thermally bonded carded web, or a web composed of fibers with diameters ranging from about 10 microns ($\mu$m) to about 100 $\mu$m. The fluorocarbon composition preferably includes a perfluoroalkyl acrylic copolymer, such as Zepel 6700®, available from DuPont. The fluorocarbon composition preferably is placed in a water-based mixture in which the fluorocarbon composition constitutes about 1% by weight of the mixture.

Two common odor absorbing reagents are activated carbon and ABSCENTS ™ (a white, crystalline synthetic molecular sieve product, sometimes referred to by the label "synthetic zeolite", available from UOP, which is a joint venture formed by Allied-Signal, Inc. and Union Carbide Corporation). Carbon has negative attributes such as dusting and difficult processability. As to the latter attribute, carbon is not soluble in fluorocarbons and thus tends to flake when its fluorocarbon mixture dries. This flaking is not desirable in a consumer product. ABSCENTS ™ is a synthetic zeolite that appears white to the naked eye, but has a high cost and is not soluble in water or other mild solvents.

Preferably, the odor absorbing reagent appears white to the naked eye. The preferred reagent is sodium bicarbonate because of its white appearance, odor absorbing effectiveness, nontoxicity and does not come loose during handling and usage. In addition, sodium bicarbonate is inexpensive. Other suitable odor absorbing reagents include: carbonates, bicarbonates, phosphates, biphosphates, sulfates, and bisulfates of alkali and alkaline earth metals; ascorbic acid, boric acid, citric acid, and maleic acid.

The cover of the present invention can be used as the cover of a sanitary pad intended to combat odors in use. Such pad preferably further includes a baffle, which is formed as a sheet that is liquid impermeable. The baffle should prevent the flow of liquids and vapors therethrough, so that vapors must pass through the odor absorbing cover in order to escape from the pad. Preferably, the materials used to form the baffle are polypropylene and/or polyethylene films. Such pad also preferably includes a mass of liquid absorbing material disposed between the cover and the baffle. The liquid absorbent material can include such materials as cellulose, wood fluff, coform materials, meltblown materials, carded materials, sphagnum moss, etc. Furthermore, structures and materials other than liquid absorbing material can be disposed between the cover and the baffle, as desired. For example, deodorant materials can be disposed in and around the liquid absorbing material or beneath liquid impermeable baffles disposed inside the sanitary pad. Moreover, these deodorant materials can be provided in sheet form or particle form.

In further accordance with the present invention, a method is provided for producing a cover for a sanitary pad. As embodied herein, a nonwoven web of material as described above is treated with a water-based liquid mixture that includes a fluorocarbon composition and at least one odor absorbing reagent. The fluorocarbon composition and odor absorbing reagents suitable for this treatment are described above and hereafter. The treated web is dried to remove the water from the mixture. The fluorocarbon composition is cured to form a hydrophobic coating around the reagent and to bind the reagent to the web. The drying and curing steps preferably are accomplished by applying a flow of heated air to the web until the water has been removed. Preferably, the air is heated in a temperature range of from about 100° C. to about 120° C., with a temperature of about 110° C. being most preferred.

The method further includes defining a plurality of apertures through the web. The apertures can be formed preferably by puncturing the web with hot pins, by treating the web with laser perforation, or by hydraulic rearrangement of the fibers. In an example of the latter alternative method of mechanically forming the apertures, the nonwoven web can be hydroentangled or hydraulically apertured using the aforementioned water/odor absorbent/fluorocarbon mixture as the fluid which mechanically forces apertures in the nonwoven web and simultaneously saturates the web with the mixture.

In a predetermined portion of the web, the number of apertures per square inch ranges from about 6 apertures to about 1100 apertures and preferably ranges from about 50 apertures per square inch to about 300 apertures per square inch. This predetermined portion of the web (a.k.a. the critical zone) preferably defines a rectangular or oblong area measuring about four inches in the lengthwise direction of the web and about 1½ inches in the widthwise direction of the web and centrally located on the surface of the web. The apertures ensure that the menstrual fluid impinging upon the outer surface of the web is quickly transferred through the web to the underlying liquid absorbent material in a sanitary pad in which the web is used as a cover. This ensures that the cover is kept as clean and dry as possible. The apertures are sized and provided in sufficient numbers per unit of web surface area in order to overcome the liquid repellent surface tension effects that are imposed by the nature of the materials preferred for forming the nonwoven web and by the presence of the hydrophobic fluorocarbon composition adhered throughout the fibers of the web.

Since the baffle of a pad is vapor impermeable, odor causing vapors cannot escape from the pad except through the cover, which is permeable to both liquid and vapor. However, in the cover of the present invention, odor absorbing reagents are disposed throughout the cover to interact with, and thereby either neutralize or remove, the odor causing vaporous molecules attempting to escape from the pad. The effectiveness of the odor absorbing reagents is assured, notwithstanding their potential exposure to the menstrual liquid passing initially through the cover. The hydrophobic coating provided by the particles of the fluorocarbon composition serves to protect the odor absorbing reagents when liquids are passing through the cover. Moreover, the same hydrophobic particles of the fluorocarbon composition do not prevent the vapor molecules from accessing the odor absorbing reagents and being removed or neutralized thereby. Accordingly, in a manner of speaking, the cover of the present invention permits the odor absorbing reagents to selectively interact with and thereby remove the odor causing vapors attempting to escape from the pad.

The accompanying drawings, which are incorporated in and constitute a part of this specification, illustrate one embodiment of the invention and, together with the description, serve to explain the principles of the invention.

DETAILED DESCRIPTION OF THE PREFERRED EMBODIMENTS

Reference now will be made in detail to the preferred embodiments of the present invention, one or more examples of which are illustrated in the accompanying drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover the modifications and variations of this invention provided they come within the scope of the appended claims and their equivalents.

Figure 1:
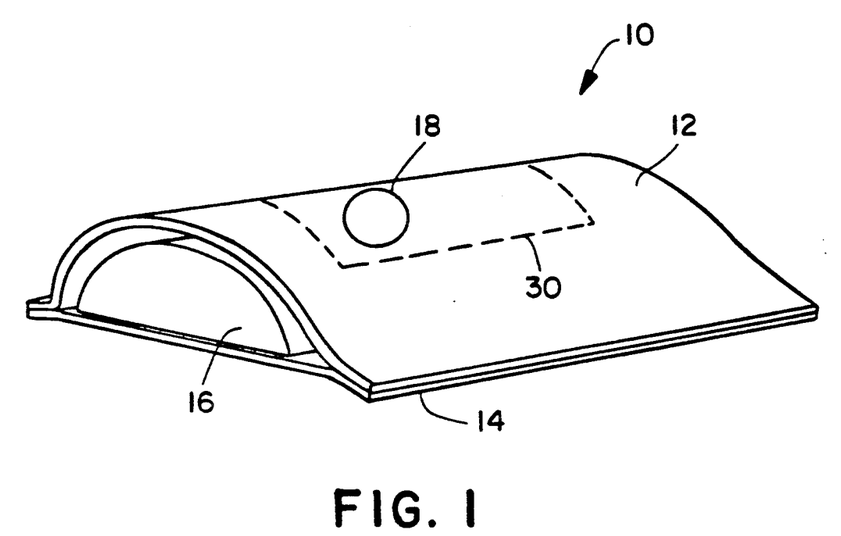
FIG. 1 illustrates a perspective view of a preferred embodiment of a sanitary pad and a cover according to the present invention.

In accordance with the present invention, a liquid permeable cover is provided. The cover can be used as a topsheet for a pad used to absorb bodily fluids. The cover of the present invention is particularly suited for controlling odor created by the presence of the bodily fluids which have been discharged from the body of the user and carried into the absorbent pad. A preferred embodiment of the cover of the present invention is shown in FIG. 1 in a sanitary pad which is represented generally by the numeral 10. The ends of pad 10 have been cut away to facilitate the description herein. As embodied herein and shown in FIG. 1 for example, a liquid permeable cover 12 forms a cover that would be positioned in contact with the body of the user of pad 10. Cover 12 can be combined with a liquid impermeable baffle 14 to surround a mass of liquid absorbent material 16 disposed between cover 12 and baffle 14. Cover 12 can be joined to baffle 14 in any of the conventional means such as heat sealing, adhesive applications, crimping, spot bonding, etc. Absorbent 16 can be constructed of any of the conventional materials used to form the liquid absorbing material of a sanitary pad. Examples of materials suitable for absorbent 16 include cellulose, wood fluff, coform materials, meltblown materials, carded materials, sphagnum moss, superabsorbent synthetic polymers, etc.

Baffle 14 preferably is formed as a film that is impermeable to the passage of both liquids and vapors therethrough. Preferably, the materials used to form baffle 14 are polypropylene and/or polyethylene. Baffle 14 can be formed by a laminate that functions to prevent the flow of liquids and vapors therethrough.

In accordance with the present invention, the cover preferably includes a nonwoven web of fibrous material. As embodied herein and shown in Figs. 1 and 2 for example, a section 18 has been removed from cover 12 of FIG. 1 and shown schematically in greater detail in FIG. 2. In order to avoid unduly complicating FIG. 2, only a small portion of a single fiber 20 is illustrated. But for this selective illustration, numerous other fibers would be visible in the schematic view shown in FIG. 2. Fiber 20 is represented in cross-section in FIG. 2 and may be any of a number of fibers or filaments which can be used to produce nonwoven webs. For example, fiber 20 can be formed preferably as a polyolefin fiber, such as a polypropylene fiber, a polyethylene fiber or a polybutylene fiber; a polyester fiber; a polyamide fiber; or a cellulosic fiber. Preferably, fibers 20 are polyolefin fibers having diameters which range from about 10 microns ($\mu$m) to about 100 $\mu$m. Fibers 20 are combined to form a nonwoven web 22 which forms cover 12. Nonwoven web 22 can be formed in a number of conventional ways, such as a spunbond web, a thermally bonded carded web, etc.

In still further accordance with the present invention, the cover includes a fluorocarbon polymer composition adhered to the fibers throughout the web. As embodied herein and shown schematically in FIG. 2 for example, three discrete masses of fluorocarbon polymer composition 24 are shown. Two are shown adhering to fiber 20 of web 22. One mass 24 is shown in cross-section in the boundary of an aperture 28 defined through web 22. For purposes of schematic illustration in FIG. 2, cross-hatching of composition 24 is intended to represent a cross-sectional view of a bead of composition 24, while the absence of cross-hatching is intended to illustrate a plan view of a bead of composition 24. A suitable fluorocarbon composition includes a perfluoroalkyl acrylic copolymer available from DuPont under the trade name Zepel 6700 and consisting of about 15% to about 20% perfluoroalkyl acrylic copolymer, about 1% to about 2% alkoxylated carboxylic acid and about 3% to about 5% ethylene glycol. Other suitable fluorocarbon compositions are polytetrafluoroethylene and SCOTCHBAND TM brand fluorocarbon composition available from 3M Company. The Zepel 6700 TM fluorocarbon composition is preferred. Preferably, a water-based mixture is prepared with about 1% by weight Zepel 6700 TM fluorocarbon composition, and the nonwoven web is dipped into this mixture and excess of the mixture can be removed by squeezing, for example. The fluorocarbon composition adheres to the fibers of the web when the web is removed from the mixture. The mixture also can be applied by spraying or other conventional coating methods.

In still further accordance with the present invention, odor absorbing reagents are bound to the web by the fluorocarbon composition and rendered hydrophobic by the composition. This fluorocarbon composition forms a coating that is liquid impermeable while remaining vapor permeable. To promote this necessary condition, the amount of fluorocarbon composition used in the mixture preferably is limited to about 1% by weight.

Examples of suitable odor absorbing reagents for practicing the present invention include one or more of the following materials: carbonates, bicarbonates, phosphates, biphosphates, sulfates, and bisulfates of alkali and alkaline earth metals; ascorbic acid, boric acid, citric acid and maleic acid. Sodium bicarbonate is the preferred odor absorbing reagent because of its non-toxic history, its white color, and its low cost.

Preferably, the odor absorbing reagent appears white under natural light to the naked eye of an observer. This is a desirable cosmetic feature of a product that is to be used in a consumer environment such as a sanitary pad. Accordingly, while activated carbon has desirable odor absorbing properties, its black color renders it less suitable for the use in applications such as the present invention.

Figure 2:
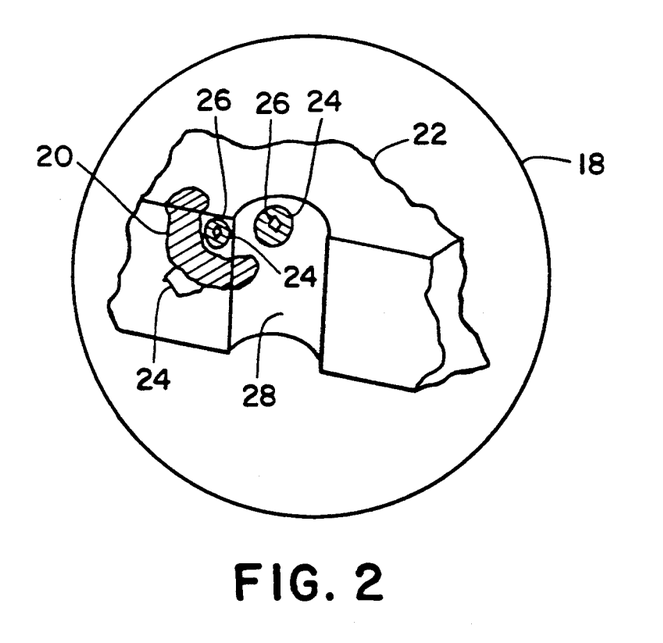
FIG. 2 schematically illustrates a perspective view taken of a detail of a section of the cover shown in FIG. 1.

As embodied herein and shown in FIG. 2 for example, an odor absorbing reagent 26 is schematically illustrated as a diamond shape being surrounded by and embedded within fluorocarbon composition particles 24, which are themselves schematically represented in cross-section so as to permit viewing of reagent 26. Preferably, reagents 26 are provided in the mixture including fluorocarbon composition 24 and are present there when the mixture is applied to web 22.

In still further accordance with the present invention, the fluorocarbon composition is cured to form a hydrophobic coating around the odor absorbing reagents and to bind the reagents to the web. As embodied herein, after the web has been treated with fluorocarbon/water/odor absorbent mixture by dipping, spraying or other conventional coating methods, for example, the web treated with the fluorocarbon composition is cured to form a hydrophobic coating around the reagent and to bind the reagent to the web. Preferably, the curing is accomplished by the step of heating the treated web. For example, such heating preferably is accomplished by blowing heated air onto the web. The air preferably is preheated to a temperature of from about 100° C. to about 120 ° C. The heated preferably is accomplished by blowing heated air onto the web. The air preferably is preheated to a temperature of from about 100° C. to about 120° C. The heated air evaporates the water and activates the fluorocarbon composition o cure same. The fluorocarbon composition adheres to the fibers of the web and surrounds and encapsulates the odor absorbing particles. Accordingly, the odor absorbing particles are bound to the web and thereafter shielded from contact with water and other liquids.

as noted above, a water-based mixture including about 1% by weight fluorocarbon composition can be applied to web 22 and can contain particles of odor absorbing reagents. Many of these odor removal capabilities of such odor absorbing reagents like activated carbon and zeolites. However, during the curing of the fluorocarbon composition by the application of heat, the web is also dried to removed the water from the mixture. Odor causing vapors are capable of penetrating through the hydrophobic coating formed by the fluorocarbon composition so that the can be absorbed by the odor absorbing reagent particles.

In yet further accordance with the present invention, a plurality of apertures are defined thought nonwoven web forming the cover. One portion of the surface of the web defines a critical zone 30 in which the number of apertures per square inch ranges from about 6 apertures to about 1100 apertures. As embodied herein and shown in FIG. 2 for example, a portion of an aperture 28 is shown defined through web 22 from one planar surface to the other. Such apertures can be formed by any of a number of methods. For example, hot pins can be thrust through web 22. In an alternative method, web 22 can e subjected to laser perforation. In yet another alternative method, the apertures are defined by subjection the web to hydraulic rearrangement. In one embodiment of the latter alternative method, the web is subjected to jets of fluid of sufficient energy to entangle or cut fibers. For example, the nonwoven web can be hydroentangled or hydraulically apertured using the aforementioned water/odor absorbent/fluorocarbon mixture as the fluid which mechanically forces apertures in the nonwoven web and simultaneously saturates the substrate with the mixture. Moreover, the provision of the apertures through cover 12 can be effected either before, during or after the application of the mixture containing the fluorocarbon composition and the odor absorbing reagents. This possibility provides some flexibility in engineering manufacturing methods for the cover and pad of the present invention.

The apertures provided in the critical zone are necessary to render the cover o the present invention, including as it does the hydrophobic particles of fluorocarbon composition, sufficiently liquid permeable so that the bodily fluids are quickly passed through cover 12 and into the underlying liquid absorbent 16. Thus, the size of the apertures, the density of the apertures, the percent of the open area in the critical zone, and the amount of fluorocarbon composition present in the nonwoven web, have been chosen so that the surface tension effects of such combination des not impede the free flow of bodily fluids through cover 12 and into liquid absorbent 16. This ensures that the cover remains clean and dry in use.

Preferably, the diameter of the apertures ranges from about 0.8 millimeters to about 10 millimeters, and more preferably in the rang of about 1 millimeter and to about 2 millimeters. Moreover, the aperture density in the critical zone preferably ranges from about 50 apertures per square inch to about 300 apertures per square inch. Furthermore, as shown in FIG. 1 for example, this aperture density pertains only to a critical zone 30 (indicated by a dashed line border), which preferably constitutes that portion of cover 12 measuring about 4 inches in the lengthwise direction of pad 10 and about 1½ inches in the widthwise direction of pad 10. Preferably, critical zone 30 defines a rectangular or oblong shape that is generally located centrally and symmetrically on the cover of the pad. Additionally, the apertures in the critical zone preferably define an open area that ranges between about 2% and about 90% of the critical zone area, and more preferably the open area formed by the apertures ranges from about 10% to about 40% of the open area of the critical zone.

By providing odor absorbing reagents in the cover of a sanitary pad, the present invention places an odor absorbing barrier at the very site where the vapors will attempt to escape from the underlying pad. Vapors from the bodily fluids flow through the cover of the present invention with the liquid into the pads liquid absorbent layers. Some of these vapors are available to be absorbed or neutralized by the odor absorbing materials residing in the cover. Before these vapors can escape from the pad by exiting through the cover, the odor absorbing materials residing in the cover "remove" the vapors by absorbing or neutralizing them. In order to place the odor absorbers at this site (i.e., the cover), they must be protected from contact with the liquid which must be allowed to pass through the cover into the underlying liquid absorbent material. The fluorocarbon composition assists in this regard by protecting the reagent from contact with liquid. The fluorocarbon composition also adheres the reagent to the web which forms the cover. In addition, the fluorocarbon composition permits the penetration of odor causing vapors past the hydrophobic fluorocarbon particles so that the vapors can interact with the odor absorbing reagents. Structures and materials other than or in addition to absorbent 16 can be disposed between cover 12 and baffle 14, as desired. For example, deodorant materials, such as those mentioned above in the Background section, can be disposed in sheet form, particle form, etc. in and around liquid absorbent 16. For example, odor absorbing reagents can be treated with a fluorocarbon composition as described above to render them repellent of the menses. The treated reagents can be evenly distributed in the liquid absorbent material to the pad. Alternatively, the treated odor absorbing reagents can form a thin layer located between cover 12 and absorbent material 16. In yet another embodiment, the treated odor absorbing reagents may form a layer located between absorbent material 16 and baffle 14. The following examples are provided as illustrations of the invention and not limitations thereof. In these examples, the odor absorbing ability of a treated web material was determined using gas chromatography head space analysis, described as follows:

A volatile mixture of 100 μl di-n-propyl sulfide, 100 μl furaldehyde, 100 μl triethylamine, and 200 μl isovaleric acid was prepared for the testing performed for Examples 1 and 2. In addition to the above ingredients included in the volatile mixture used to test Examples 1 and 2, the volatile mixture prepared for the testing conducted for Example 3 included an additional 100 μl of pyridine. A 10 μl volume of the respective volatile mixture was added by a pipetman, to a 40 milliliter Environmental Protection Agency (EPA) standard sample vial and sealed with a mininert screw cap. This serves as a blank to ensure the presence of all components of the mixture.

A known quantity of cover material to be tested (in out examples 250 milligrams) is placed in a 40-ml EPA vial. After the addition of 10 μl of the appropriate volatile mixture described above, the vial is sealed with a mininert screw cap and is incubated at 37° C. for 2 hours for Examples 1 & 2 and 3½ hours for Example 3. (When testing a sheet form, an untreated sheet can be used as the control, and in such case is run under the same conditions). After the allotted incubation period, a 10 microliter head space sample from each vial is injected into a Hewlett Packard 5890 ™ gas chromatograph using the following parameters:

| | |
|---|---|
| Initial Time = | 1.00 minutes |
| Initial Temp. = | 35° C. |
| Ramp Rate = | 10°/minute |
| Final Temp. = | 75° C. |
| Final Time = | 0.15 minutes |
| Inj. B = | 175° C. |
| Det. B = | 300° C. |
| Oven Max. = | 300° C. |
| Equib. Time = | 0.15 minutes |
| Flow B (He) = | 15.0–16.0 milliliters per minute |
| Range (Sig. 1) = | 4 |
| Zero (Sig. 1) = | 2 |
| Attn. (Sig. 1) = | 2 |

A Hewlett Packard 3390 A ™ integrator was used to record the area count at the retention time of each of the five volatile components, and the percent absorption was calculated according to the following formula in which: X = the total area under the peak recorded by the integrator for the blank; Y = the total area under the peak recorded by the integrator for the sample.

$$\text{The percent absorption} = \frac{X - Y}{X} \times (100).$$

In Examples 1, 2 and 3, area count numbers for the blank were used as the base numbers to calculate the percent absorption rather than using the area count numbers obtained in testing a control (untreated) web.

A control (untreated) web was not run for Examples 1 and 2. However, a control web was tested for Example 3, and the results of this test are presented following Example 3.

EXAMPLE 1

One gram of a molecular sieve (synthetic zeolite) sold by UOP Corporation under the name SMELL-RITE ™ was added to 100 milliliters of 1% solution of Zepel 6700 TM. This 1% solution is 99% by weight water and 1% by weight fluorocarbon composition suspended in the water. This solution was stirred thoroughly to disperse the zeolite. A polypropylene spunbonded web having a basis weight of 0.6 ounces per square yard was prepared by forming apertures in a central strip along the web. The aperture pattern consists of an aperture diameter of 1.37 millimeters, a hole density of 90 holes per inch squared, and a percent open area of 20. This web then was dipped into the suspension, and excess solution was squeezed out of the web. A flow of air heated to a temperature of 110° C. was applied to the web until the web had dried. The odor absorption performance of the treated web was evaluated by the above-described gas chromatography head space analysis method. About 0.25 grams of the treated web was exposed to 0.01 milliliters of a solution containing known volatiles for two hours. These volatiles were selected as representative of the odor causing volatiles present in menstrual fluid. The percentages of the volatiles removed by the treated web (the percent absorption) are given as follows: triethylamine 88%; furaldehyde 59%; isovaleric acid 95%; di-n-propyl sulfide 78%. As noted above, pyridine was not among the volatiles included in the test solution for this example.

EXAMPLE 2

One gram of baking soda supplied by Church & Dwight Co., Inc., was dissolved in 100 milliliters of solution containing 1% by weight Zepel 6700 TM. The spunbonded web described in Example 1 was treated with the solution by the technique mentioned in Example 1. The treated web was evaluated by the method detailed above. The percentage of volatiles removed by the treated web (the percent absorption) are given as follows: triethylamine 48%; furaldehyde 32%; isovaleric acid 95%; di-n-propyl sulfide 76%. As noted above, pyridine was not among the volatiles included in the test solution for this example.

EXAMPLE 3

Six grams of SMELLRITE TM synthetic zeolite, sold by UOP, was added to 300 milliliters of a mixture including water and 1% by weight of Zepel 6700 TM. The mixture was stirred to disperse the zeolite. The web was treated as described in Example 1. The percentages of volatiles removed by the treated web (the percent absorption) are given as follows:

| | |
|---|---|
| triethylamine | 44% |
| pyridine | 43% |
| furaldehyde | 36% |
| isovaleric acid | −412% |
| di-n-propyl sulfide | 68% |

A negative number indicates that the component was not removed. This can occur in a multichemical sample because the absorption of one component can result in a release of another component by shifting the chemical equilibrium.

The control (untreated) web removed the following percentage of volatiles:

| | |
|---|---|
| triethylamine | 14% |
| pyridine | 29% |
| furaldehyde | 0% |
| isovaleric acid | −243% |
| di-n-propyl sulfide | 63% |

What is claimed is:

1. A pad for absorbing bodily fluids and controlling odor created by the presence of the bodily fluids in the pad, the pad comprising:
   (a) a liquid ad vapor permeable cover having a periphery, the cover including:
      (i) a nonwoven web having a zone wherein from about 6 to about 1100 apertures are defined by the web within the zone;
      (ii) a liquid impermeable and vapor permeable fluorocarbon composition adhered to said web, and
      (iii) an odor absorbing reagent bound to said web by said fluorocarbon composition, said reagent being rendered hydrophobic by said composition;
   (b) a liquid and vapor impermeable baffle having a periphery; and
   (c) a liquid absorbent material disposed between said cover and said baffle; and
   wherein the cover and the baffle are in general juxtaposed position with respect to each other and are joined to each other at their respective peripheries.

2. The pad according o claim 1, wherein the nonwoven web is formed from fibers selected from the group consisting of polyester fibers, polyamide fibers, cellulosic fibers or polyolefin fibers.

3. The pad according to claim 1, wherein the liquid impermeable and vapor permeable fluorocarbon composition is selected from the group consisting of perfluoroalkyl acrylic copolymer or polytetrafluoroethylene.

4. The pad according to claim 1, wherein h odor absorbing material is selected from the group consisting of one or more of carbonates, bicarbonates, phosphates, biphosphates, sulfates, and bisulfates of alkali and alkaline earth metals, ascorbic acid, boric acid, citric acid and maleic acid.

5. The pad according to claim 1, wherein the liquid and vapor impermeable baffle is formed from a film selected from the group consisting of polypropylene or polyethylene film.

6. The pad according o claim 1, wherein the liquid absorbent material is selected from the group consisting of cellulose, wood fluff, coform materials, meltblown materials, carded materials or sphagnum moss.

7. The pad according to claim 1, wherein the diameter of the apertures ranges from about 0.8 millimeters to about 10 millimeters.

8. The pad according to claim 7, wherein the diameter of the apertures ranges rom about 1 millimeter to about 2 millimeters.

9. The pad according to claim 1, wherein the aperture density in the zone ranges from about 50 apertures per square inch to about 300 apertures per square inch.

10. The pad according to claim 9, wherein the zone is about 4 inches by 1.5 inches.

11. The pad according to claim 10, wherein the zone is generally located centrally and symmetrically on the cover.

12. The pad according to claim 11, wherein the apertures define an open area that ranges from about 2% to about 90% of the zone.

13. The pad according to claim 12, wherein the apertures define an open area that ranges from about 10% to about 40% of the open area of the zone.

14. The pad of claim 1, wherein the cover and the baffle are joined at their respective peripheries by a means selected from h group consistin of heat sealing, adhesive application, crimping or spot bonding.

15. A pad for absorbing bodily fluids and controlling odor created by the presence of the bodily fluids in the pad, the pad comprising:
   (a) a liquid and vapor permeable cover having a periphery, the cover including:
      (i) a nonwoven web having a zone wherein from about 6 to about 1100 apertures per square inch are defined by the web within the zone;
      (ii) a liquid impermeable and vapor permeable fluorocarbon composition adhered to said web, and
      (iii) odor absorbing means bound to the web by the fluorocarbon composition, the reagent being rendered hydrophobic by the composition;
   (b) a liquid and vapor impermeable baffle having a periphery; and
   (c) a liquid absorbent material disposed between said cover and said baffle; and
   wherein the cover and the baffle are in general juxtaposed position with respect to each other and are joined to each other at their respective peripheries.

16. The pad according to claim 15, wherein the nonwoven web is formed from fibers selected from the group consisting of polyester fibers, polyamide fibers, cellulosic fibers or polyolefin fibers.

17. The pad according to claim 15, wherein the liquid impermeable and vapor permeable fluorocarbon composition is electrode from the group consisting of perfluoroalkyl acrylic copolymer or polytetrafluoroethylene.

18. The pad according to claim 15, wherein the odor absorbing material is selected from the group consisting of one or more of carbonates, bicarbonates, phosphates, biphosphates, sulfates, and bisulfates of alkali and alkaline earth metals, ascorbic acid, boric acid, citric acid and maleic acid.

19. The pad according to claim 15, wherein the liquid and vapor impermeable baffle is formed from a film selected from the group consisting of polypropylene or polyethylene film.

20. The pad according to claim 15, wherein the liquid absorbent material is selected from the group consistin of cellulose wood fluff, coform materials, meltblown materials, carded materials or sphagnum moss.

21. The pad according to claim 15, wherein the diameter of the apertures ranges from about 0.8 millimeters to about 10 millimeters.

22. The pad according to claim 21, wherein the diameter of the apertures ranges from about 1 millimeter to about 2 millimeters.

23. The pad according to claim 15, wherein the aperture density in the zone ranges from about 50 apertures per square inch to about 300 apertures per square inch.

24. The pad according to claim 23, wherein the zone is about 4 inches by 1.5 inches.

25. The pad according to claim 24, wherein the zone is generally located centrally and symmetrically on the cover.

26. The pad according to claim 25, wherein the apertures define an open area that ranges from about 2% to about 90% of the zone.

27. The pad according to claim 26, wherein the apertures define an open area that ranges from about 10% to about 40% of the open area of the zone.

28. A pad for absorbing bodily fluids and controlling odor created by the presence of the bodily fluids in the pad, the pad comprising:
   (a) a liquid and vapor permeable cover having a periphery, the cover including:
      (i) a nonwoven web formed from fibers selected from the group consisting of polyester fibes, polyamide fibers, cellulosic fibers or polyolefin fibers the nonwoven web having a zone wherein from about 6 to about 1100 apertures per square inch are defined by the web within the zone;
      (ii) a liquid impermeable and vapor permeable fluorocarbon composition selected from the group consisting of perfluoroalkyl acrylic copolymer or polytetrafluoroethylene adhered to said web; and
      (iii) odor absorbing material, selected from the group consisting of one or more of carbonates, bicarbonates, phosphates, biphosphates, sulfates d bisulfates of alkali and alkaline earth metals, ascorbic acid, boric acid, citric acid and maleic acid, bound to the web by the fluorocarbon composition, the reagent being rendered hydrophobic by the composition;
   (b) a liquid and vapor impermeable baffle having a periphery, the baffle being formed from a film selected from the group consisting of polypropylene or polyethylene film; and
   (c) a liquid absorbent material, selected from the group consisting of cellulose, wood fluff, coform materials, meltblown materials, carded materials or sphagnum moss, disposed between the cover and the baffle; and
   wherein the cover and the baffle are in general juxtapose position with respect to each other and are joined to each other at their respective peripheries.

29. The pad according to claim 28, wherein the diameter of the apertures ranges from about 0.8 millimeters to bout 10 millimeters.

30. The pad according to claim 29, wherein the diameter o the apertures ranges from about 1 millimeter to about 2 millimeters.

31. The pad according to claim 28, wherein the aperture density in the zone ranges from about 50 apertures per square inch to about 300 apertures per square inch.

32. The pad according to claim 31, wherein the zone is about 4 inches by 1.5 inches.

33. The pad according to claim 32, wherein the zone is generally located centrally and symmetrically on The cover.

34. The pad according to claim 33, wherein the apertures define an open area that ranges from about 2% to about 90% of the zone.

35. The pad according to claim 34, wherein the apertures define an open area that ranges from about 10% to about 40% of the open area of the zone.

* * * * *